United States Patent [19]

Husbands

[11] 4,064,165
[45] Dec. 20, 1977

[54] 15-ETHYNYL-PGE$_1$

[75] Inventor: George E. M. Husbands, Philadelphia, Pa.

[73] Assignee: American Home Products Corporation, New York, N.Y.

[21] Appl. No.: 717,725

[22] Filed: Aug. 25, 1976

Related U.S. Application Data

[62] Division of Ser. No. 568,212, April 14, 1975, Pat. No. 4,001,314.

[51] Int. Cl.$^2$ ............................................. C07C 177/00
[52] U.S. Cl. ................................. 260/514 D; 560/121
[58] Field of Search ....................... 260/468 D, 514 D

[56] References Cited

U.S. PATENT DOCUMENTS

| | | | |
|---|---|---|---|
| 3,922,302 | 11/1975 | Strike | 260/514 |
| 4,001,314 | 1/1977 | Husbands | 260/514 |

*Primary Examiner*—Robert Gerstl
*Attorney, Agent, or Firm*—Robert Wiser

[57] ABSTRACT

7-(2β-[(3S)-3-Ethynyl-3-hydroxy-trans-1-octenyl]-3α-hydroxy-5-oxo-1α-cyclopentyl)-cis-5-heptenoic acid, 2β-[(3S)-3-ethynyl-3-hydroxy-trans-1-octenyl]-3α-hydroxy-5-oxo-1α-cyclopentane heptanoic acid, related compounds, and intermediates thereto are disclosed. The final products have activity as bronchodilators and in reducing gastric secretion.

3 Claims, No Drawings

15-ETHYNYL-PGE₁

This is a division of application Ser. No. 568,212 filed Apr. 14, 1975 now U.S. Pat. No. 4,001,314.

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as bronochodilation, the ability to reduce gastric secretion, to modify muscle tone, as well as the ability to raise or lower blood pressure.

The present invention concerns 15-ethynyl-11,15-dihydroxy-9-oxo-prostaglandines and intermediates thereto.

DESCRIPTION OF THE INVENTION

The invention sought to be patented in its first composition aspect resides in the concept of a chemical compound of the structure.

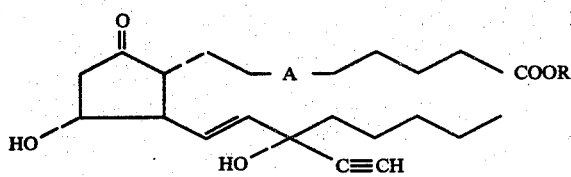

wherein A is a single bond or a cis double bond, R is hydrogen, alkyl of from 1 up to about 6 carbon atoms, alkali metal, or a pharmacologically acceptable cation derived from ammonia or a basic amine.

The tangible embodiments of the first composition aspect of the invention in the free acid form possess the inherent general physical property of being substantially insoluble in water, and generally soluble in such organic solvents as methylene chloride, and ethyl acetate. Examination of compounds produced according to the hereinafter described process reveals, upon infrared, nuclear magnetic resonance, and mass spectrographic analyses, spectral data supporting the molecular structures herein set forth. The aforementioned physical characteristics, taken together with the nature of the starting materials, and the mode of synthesis confirm the structure of the compositions sought to be patented.

The tangible embodiments of the first composition aspect of the invention possess the inherent applied use characteristic of exerting bronchodilating effects and reducing gastric secretion upon administration to warm-blooded animals as evidenced by pharmacological evaluation according to standard test procedures.

The invention sought to be patented in a first subgeneric aspect of the first composition aspect of the invention resides in the concept of a compound of formula I wherein A is a cis double bond.

The invention sought to be patented in a second subgeneric aspect of the first composition aspect of the invention resides in the concept of a compound of formula I wherein A is a single bond.

The invention sought to be patented in a second composition aspect resides in the concept of a chemical compound of the formula:

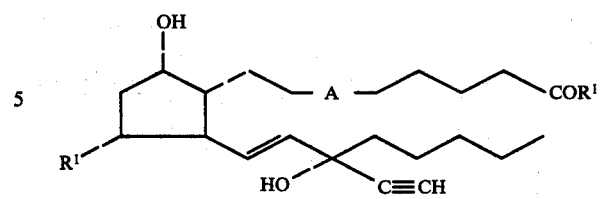

wherein R¹ is hydroxy or trimethylsilyloxy and A is as defined hereinabove.

The tangible embodiments of the second composition aspect of the invention possess the inherent general physical properties of being substantially insoluble in water, and are generally soluble in organic solvents such as ethyl acetate and ether.

Examination of the compound produced according to the hereinafter described process reveals upon infrared, nuclear magnetic resonance, and mass spectrographic analysis, spectral data supporting the molecular structure herein set forth. The aforementioned physical characteristics, taken together with the nature of the starting materials, and the mode of synthesis, confirm the structure of the compositions sought to be patented.

The tangible embodiments of the second composition aspect of the invention possess the inherent applied use characteristic of being intermediates in the synthesis of compounds of formula I.

The invention sought to be patented in a first subgeneric aspect of the second composition aspect resides in the concept of a chemical compound which is 7-(2β-[(3S)-3-ethynyl-3-hydroxy-trans-1-octenyl]-5α-hydroxy-3α-trimethylsilyloxy-1α-cyclopentyl)-cis-5-heptenoic acid, trimethylsilyl ester.

The invention sought to be patented in a second subgeneric aspect of the second composition aspect of the invention resides in the concept of a chemical compound which is 7-(2β-[(3S)-3-ethynyl-3-hydroxy-trans-1-octenyl]-3α,5α-dihydroxy-1α-cyclopentyl)-cis-5-heptenoic acid.

The invention sought to be patented in a third subgeneric aspect of the second composition aspect resides in the concept of a chemical compound which is 2β-[(3S)-3-ethynyl-3-hydroxy-trans-1-octenyl]-5α-hydroxy-3α-trimethylsilyloxy-1α-cyclopentane heptanoic acid, trimethylsilyl ester.

The invention sought to be patented in a fourth subgeneric aspect of the second composition aspect of the invention resides in the concept of a chemical compound which is 2β-[(3S)-3-ethynyl-3-hydroxy-trans-1-octenyl]-3α,5α-dihydroxy-1α-cyclopentane heptanoic acid.

The invention sought to be patented in its process aspect resides in the concept of a method of relieving bronchial spasm and facilitating breathing in warm-blooded animals which comprises administering to a warm-blooded animal in need thereof an amount sufficient to relieve bronchial spasm and facilitate breathing in said warm-blooded animal a chemical compound of the formula I.

DESCRIPTION OF THE PREFERRED EMBODIMENTS

The compositions of the invention may be prepared by a number of routes. 7-(2β-[(3S)-3-ethynyl-3-hydroxy-trans-1-octenyl]-3α,5α-dihydroxy-1α-cyclopentyl)-cis-5-heptenoic acid (II) may be prepared by treating the tris-(trimethylsilyl) derivative of 15-oxo-PGF$_{2\alpha}$, as described in U.S. Pat. No. 3,804,889 with ethynyl Grignard reagent, conveniently prepared from acetylene and methyl magnesium bromide, in a suitable solvent, conveniently a mixture of tetrahydrofuran and diethylether, at elevated temperature, conveniently at reflux, in the presence of excess acetylene, followed by separation of II by standard means from the hydrolyzed reaction product, conveniently by chromatography on silica gel.

Compound II may also be prepared by treating 15-oxo-PGF$_{2\alpha}$, also described in U.S. Pat. No. 3,804,889 with ethynyl Grignard reagent, conveniently prepared from acetylene and methylmagnesium bromide, in a suitable solvent, conveniently a mixture of diethylether and tetrahydrofuran, at reduced temperature initially, conveniently at about 0° C. and then at moderate temperature, conveniently at room temperature, followed by separation of II by standard means from the crude reaction product, conveniently by chromatography on silica gel. 7-(2$\beta$-[(3S)-3-ethynyl-3-hydroxy-trans-1-octenyl]-5$\alpha$-hydroxy-3$\alpha$-trimethylsilyloxy-1$\alpha$-cyclopentyl)-cis-5-heptenoic acid, trimethylsilylester (III) may be prepared by treating II in a suitable solvent, conveniently acetone with trimethylsilyl diethylamine at reduced temperature, conveniently about $-45°$ C. to about $-35°$ C. 7-(2$\beta$-[(3S)-3-ethynyl-3-hydroxy-trans-1-octenyl]-3$\alpha$-hydroxy-5-oxo-1$\alpha$-cyclopentyl)-cis-5-heptenoic acid (Ia) may be prepared from compound II directly or from compound III. Treatment of compound III with the Collins modification of the Sarett reagent at moderate temperature, conveniently room temperature, in solution, conveniently in methylene chloride, followed by isolation of the desired product by standard techniques from the hydrolyzed reaction mixture gives Ia. Chromatography on silica gel is a convenient method. If II in acetone solution is treated with Jones reagent at reduced temperature, conveniently about $-35°$ C., compound Ia may be separated from the reaction product by standard techniques. Chromatography on silica gel is a convenient method.

Similar procedures may be used to prepare 2$\beta$-[(3S)-3-ethynyl-3-hydroxy-trans-1-octenyl]-3$\alpha$,5$\alpha$-dihydroxy-1$\alpha$-cyclopentane heptanoic acid (IV), 2$\beta$-[(3S)-3-ethynyl-3-hydroxy-trans-1-octenyl]-5$\alpha$-hydroxy-3$\alpha$-trimethylsilyloxy-1$\alpha$-cyclopentane heptanoic acid trimethylsilyl ester (V), and 2$\beta$-[(3S)-3-ethynyl-3-hydroxy-trans-1-octenyl]-3$\alpha$-hydroxy-5-oxo-1$\alpha$-cyclopentane heptanoic acid (Ib).

Compound IV may be prepared in a fashion similar to that described for compound II employing the tris-trimethylsilyl derivative of 15-oxo-PGF$_{1\alpha}$, prepared from 15-oxo-PGF$_{1\alpha}$ as described in U.S. Pat. No. 3,849,487 by the methods described in U.S. Pat. No. 3,804,889 for the preparation of the tris-trimethylsilyl derivative of PGF$_{2\alpha}$. Compound V may be prepared from compound IV by treating compound IV in a solvent, conveniently acetone, at reduced temperature, conveniently about $-40°$, with a trimethylsilylating agent, conveniently trimethylsilyl diethylamine. If desired V may be recovered from the reaction by standard techniques. Addition of methanol and evaporation of solvent at room temperature is a convenient technique. Compound Ib may be prepared from compound V in a fashion similar to that described for the preparation of compound Ia from compound III.

The esters of formula I (R is alkyl) are prepared by standard methods, such as for example, by treating a solution of the free acids with diazomethane or other appropriate diazohydrocarbons, such as diazoethane, 1-diazo-2-ethylpentane, and the like. The alkali metal carboxylates of the invention can be prepared by mixing stoichiometrically equivalent amounts of the free acids of formula I, preferably in aqueous solution, with solutions of alkali metal bases, such as sodium, potassium, and lithium hydroxides of carbonates, and the like, then freeze drying the mixture to leave the product as a residue. The amine salts can be prepared by mixing the free acids, preferably in solution, with a solution of the appropriate amine, in water, isopropanol, or the like, and freeze drying the mixture to leave the product as a residue.

The term "alkyl of from about 1 to about 6 carbon atoms" when used herein and in the appended claims includes straight and branched chain hydrocarbon radicals, illustrative members of which are methyl, ethyl, n-propyl, i-propyl, n-butyl, t-butyl, n-pentyl, n-hexyl, 3-methylpentyl, 2,3-dimethylbutyl, and the like. "Alkali metal" includes, for example, sodium, potassium, lithium, and the like. A "pharmacologically-acceptable cation derived from ammonia of a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

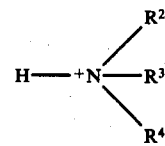

wherein R$^2$, R$^3$, and R$^4$, independently, are hydrogen, alkyl of from about 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms, or, when taken together with the nitrogen atom to which they are attached, any two of R$^2$, R$^3$, and R$^4$ form part of a 5 to 6-membered heterocyclic ring containing carbon, hydrogen, oxygen, or nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethylidiethanolammonium, n-butylmonoethanolammonium, tris(hydroxymethyl)methylammonium, phenylmonoethanolammonium, and the like.

In practicing the method of the invention, the instant compositions can be administered in a variety of dosage forms, the oral route being used primarily for maintenance therapy while injectables tend to be more useful in acute emergency situations. Inhalation (aerosols and solution for nebulizers) seems to be somewhat faster acting than other oral forms slower than injectables and this method combines the advantages of maintenance and moderately-acute stage therapy in one dosage unit.

The daily dose requirements vary with the particular compositions being employed, the severity of the symptoms being presented, and the animal being treated. The dosage varies with the size of the animal. With large animals (about 70 kg. body weight), by the oral inhalation route, with for example a hand nebulizer or a pressurized aerosol dispenser the dose is from about 1 microgram to about 50 micrograms, and preferably from about 1 to about 25 micrograms, approximately every four hours, or as needed. By theoral ingestion route, the effective dose is from about 0.1 to about 2 mg., preferably from about 0.5 to about 15 mg. up to a total of about 40 mg. per day. By the intravenous route, the ordinarily effective dose is from about 50 micrograms to about 30 micrograms, preferably about 20 micrograms per day.

For unit dosages, the active ingredient can be compounded into any of the usual oral dosage forms including tablets, capsules and liquid preparation such as elixirs and suspensions containing various coloring, flavoring, stabilizing and flavor masking substances. For compounding oral dosage forms the active ingredient can be diluted with various tableting materials such as starches of various types, calcium carbonate, lactose, sucrose and dicalcium phosphate to simplify the tableting and capsulating process. A minor proportion of magnesium stearate is useful as a lubricant. In all cases, of course, the proportion of the active ingredient in said composition will be sufficient to impart bronchadilating activity thereto. This will range upward from about 0.0001% by weight of active ingredient in said composition.

For administration by the oral inhalation route with conventional nebulizers or by oxygen aerosolization it is convenient to provide the instant active ingredient in dilute aqueous solution, preferably at concentrations of about 1 part of medicament to form about 100 to 200 parts by weight of total solution. Entirely conventional additives may be employed in stabilize these solutions or to provide isotonic media, for example, sodium chloride, sodium citrate, citric acid, sodium bisulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with co-solvent, such as ethanol, flavoring materials and stabilizers. Instead of a co-solvent there can also be used a dispersing agent such as oleyl alcohol. Suitable means to employ the aerosol inhalation therapy technique are described fully in U.S. Pat. Nos. 2,868,691 and 3,095,355, for example.

The following examples further illustrate the best mode contemplated by the inventor for the practice of the invention:

EXAMPLE 1

7-(2β-[(3S)-3-Ethynyl-3-Hydroxy-Trans-1-Octenyl]-3α,5α-Dihydroxy-1α-Cyclopentyl)-Cis-5-Heptenoic Acid.

Equip a flask with a magnetic stirrer, condenser and a gas inlet tube charge the flask with dry tetrahydrofuran (66 ml.) and 3 M ethereal methyl magnesium bromide (30 ml.). Bubble purified acetylene through the stirred solution for 2.5 hours, then add a solution of the tris(trimethylsilyl) derivative of 15-oxo-PGF$_{2\alpha}$ (1.0 g.), in dry tetrahydrofuran (70 ml.). Reflux gently with stirring under acetylene for 3 hours and let stand at room temperature overnight. Pour the reaction into 20% ammonium chloride solution and extract with ethyl acetate. Wash, dry and evaporate the extract in vacuo to obtain 1.5 grams of crude material. Treat this crude with a mixture of ethanol (50 ml.) and water (50 ml.) and stir at room temperature for 4 hours. Then add brine and extract the mixture with ethyl acetate. Wash with brine, dry and evaporate the extract to obtain a light brown oil, 0.740 g.

Chromatograph the mixture on 150 grams of Mallinckrodt Silicar CC4 silica gel and elute successively with 700 ml. of 50%, 600 ml. of 60%, 600 ml. of 70% and 800 ml. of 80% ethyl acetate in hexane, collecting the corresponding eluates in 100 ml. fractions. The progress of the chromatography is followed with thin layer chromatography using chloroform:methanol:acetic acid (80:10:10). Fractions 24 to the end are combined to give the title product (60 mg.). I. R. Analysis: $\lambda_{max}^{film}$ 3.05, 3.4, 5.8, 6.8, 7.1, 8.1, 10.3, 13.2 μ. NMR Analysis: Signals at δ=0.9 (triplet, 3p, 20—CH$_3$), 2.5 (singlet, 1p, —C CH), 4.15 (multiplet, 2p, 9 + 11-H), 5.3 (doublet, 2p, 5 + 6H), 5.75 (doublet, 3p, 13, 14-H + —OH) ppm.

Mass Spectral Analysis: M+ Calc. for tetratrimethylsilyl derivative m/e 666 M+Found m/e 666.

EXAMPLE 2

7-(2β-[(3S)-3-Ethynyl-3-Hydroxy-Trans-1-Octenyl]-5α-Hydroxy-3α-Trimethylsilyloxy-1α-Cyclopentyl)-Cis-5-Heptenoic Acid, Trimethylsilylester Dissolve 7-(2β-[(3S)-3-ethynyl-3-hydroxy-trans-1-octenyl]-3α,5α-dihydroxy-1α-cyclopentyl)-cis-5-heptenoic acid (1 g.) in acetone (40 ml.) and cool to −40°. Add trimethylsilyl diethylamine (4 ml.) and maintain the temperature of the solution between −35° C. for 2 hours. Add diethyl ether (300 ml.) precooled to −78° and wash the solution with cold aqueous sodium bicarbonate solution. Wash the ether phase with brine, dry over sodium sulfate and evaporate to obtain the title product is sufficient purity for further synthetic work (990 mg.).

EXAMPLE 3

7-(2β-[(3S)-3-Ethynyl-3-Hydroxy-Trans-1-Octenyl]-3α-Hydroxy-5-Oxo-1α-Cyclopentyl)-Cis-5-Heptenoic Acid Prepare Collins Modification of the Sarett Reagent by adding chromium trioxide (2.0 g.) to a well stirred solution of pyridine (3.2 ml.) in methylene chloride (100 ml.) and stir for fifteen minutes. Add the 7-(2β-[(3S)-3-ethynyl-3-hydroxy-trans-1-octenyl]-5α-hydroxy-3α-trimethylsilyloxy-1α-cyclopentyl)-cis-5-heptenoic acid, trimethylsilylester (990 mg.) in a minimum of methylene chloride and stir for 30 minutes. Filter and add sufficient ethyl acetate to render the organic phase lighter than water. Wash the organic phase with brine, dry and evaporate to obtain a red oil, 100 mg. Dissolve the oil in a mixture of methanol (50 ml.) and water (25 ml.) and stir overnight. Evaporate the solvent. Add brine and extract with ethyl acetate. Wash, dry and evaporate the extract to obtain an oil, 100 mg.

Chromatograph the oil on 10 g. Mallinckrodt Silicar CC4 silica gel and elute successively with 130 ml. of 50% ml. 55% ethyl acetate in hexane, collecting the corresponding eluates in 10 ml. fractions follow the progress of the chromatography with thin layer chromatography using chloroform-methanol-acetic acid (80:10:10). Combine fractions 11 and 12 to obtain the title product, 44 mg.

Mass spectral Analysis: Calc. for tetratrimethylsilyl derivatives M+ at m/e 664 Found: M+ at m/e 664.

EXAMPLE 4

7-(2β-[(3S)-3-Ethynyl-3-Hydroxy-Trans-1-Octenyl]-3α,5α-Dihydroxy-1α-Cyclopentyl)-Cis-5-Heptenoic Acid Add dry tetrahydrofuran (400 ml.) to a flask equipped with a gas inlet tube and saturated it with purified acetylene gas. Add a solution of 3M ethereal methyl magnesium bromide (40 ml.) in dry tetrahydrofuran (100 ml.) dropwise and stir for 40 minutes. Cool in ice and add a solution of 15-oxo-$PGF_{2\alpha}$(2.7 g.) in dry tetrahydrofuran (200 ml.) rapidly dropwise. Stir the resulting mixture at room temperature for 2 hours. Cool in ice and add saturated ammonium chloride. Separate the layers, acidify the aqueous layer with acetic acid and extract it with ether. Combine the organic phases, wash with brine, decolorize using charcoal, dry over magnesium sulfate and evaporate to obtain a product (2.96 g.).

Chromatograph the product on Mallinckrodt Silicar CC4 silica gel (250 g.) and elute successively with 2.2 liters of 60%, and 600 ml. of ethyl acetate in hexane collecting the corresponding eluates in 200 ml. fractions. Continue the chromatography by eluting successively with 400 ml. of 65% and 1 liter of 70% ethyl acetate in hexane, collecting the corresponding eluates in 100 ml. fractions. Combine fractions 18-28 to obtain the title product (680 mg.).

EXAMPLE 5

7-(2β-[(3S)-3-Ethynyl-3-Hydroxy-Trans-1-Octenyl]-3α-Hydroxy-5-Oxo-1α-Cyclopentyl)-Cis-5-Heptenoic Acid Dissolve 7-(2β-[(3S)-3-ethynyl-3-hydroxy-trans-1octenyl]-3α,5α-dihydroxy-1α-cyclopentyl)-cis-5-heptenoic acid (670 mg.) in acetone (200 ml.) and cool it under nitrogen to −35° C. Add Jones reagent (0.4 ml.) dropwise rapidly. Stir for 1 hour at −35° C. and check the progress of the reaction by thin layer chromatography using ethyl acetate-acetic acid-2,2,4-trimethyl pentane-water (90:20:50:100) organic phase as the developing system. Add a further 0.3 ml.) of Jones reagent and stir for another hour at −35° C. Add isopropanol and filter the mixture at 0° C. Evaporate the solvent in vacuo at room temperature, Dissolve the residue in methylene chloride, wash with brine, dry over magnesium sulfate and evaporate to obtain 480 mg. of a crude product.

Chromatograph the crude product on Mallinckrodt Silicar CC4 silica gel (50 g.) and elute successively with 350 ml. of 30% and 100 ml. of 40% ethyl acetate in hexane, collecting 100 ml. fractions, followed by 300 ml. of 40%, 650 ml. of 50% and 400 ml. of 60% ethyl acetate in hexane, collecting the corresponding eluates in 50 ml. fractions. Follow the progress of the chromatography using thin layer chromatography (as above). Combine fractions 18-21 to obtain the title product (74 mg.). I. R. Analysis: $\lambda_{max}^{film}$ 3.05, 3.4, 5.75, 7.2, 8.0, 8.6, 9.3, 10.2 μ. NMR Analysis: Signals at δ=0.9 (triplet, 3p, $CH_3$), 2.59 (singlet, 1p, C≡CH), 4.15 (1p, 11-H), 5.4 (2p, 5 and 6-H), 5.75 (3p, 13 and 14-H and OH) ppm.

Mass Spectral Analysis: Calc. for tetratrimethylsilyl derivative M+ at m/e 664 Found: M+ at m/e 664.

EXAMPLE 6

2β-[(3S)-3-Ethynyl-3-Hydroxy-Trans-1-Octenyl]-3α,-5α-Dihydroxy-1α-Cyclopentane-Heptanoic Acid Following the procedures of Example 1 there is obtained from the tris trimethylsilyl derivative of 15-oxo-$PGF_{1\alpha}$, the title product m.p. 112°-114° C.

Mass Spectral Analysis: Calc. for tetratrimethylsilyl derivative M+ at m/e 668 Found: M+ at m/e 668.

EXAMPLE 7

2β-[(3S)-3-Ethynyl-3-Hydroxy-Trans-1-Octenyl]-5α-Hydroxy-3α-Trimethylsilyloxy-1α-Cyclopentane-Heptanoic Acid Dissolve 2β-[(3S)-3-ethynyl-3-hydroxy-trans-1-octenyl]-3α,5α-dihydroxy-1α-cyclopentane heptanoic acid (600 mg.) in dry acetone and cool to −40° C. Add trimethylsilyldiethylamine (5 ml.) dropwise and maintain the temperature of the solution between −40° and −45° C. for 2 hours. Add methanol (10 ml.) and evaporate the solvents at room temperature. Dry the residue under vacuum.

EXAMPLE 8

2β-[(3S)-3-Ethynyl-3-Hydroxy-Trans-1-Octenyl]-3α-Hydroxy-5-Oxo-1α-Cyclopentane Heptanoic Acid Following the procedure of Example 3 there is obtained from 2β-[(3S)-3-ethynyl-3-hydroxy-trans-1-octenyl]-5α-hydroxy-3α-trimethylsilyloxy-1α-cyclopentane heptanoic acid the title product, m.p. 85°-87° C.

Mass Spectral Analysis: Calc. for tetratrimethylsilyl derivative M+ at m/e 666 Found: M+ at m/e 666.

EXAMPLE 9

Anesthetized (Dial-urethane) guinea pigs were artificially respired at a constant positive air pressure (Starling miniature pump) and changes in tidal air during inspiration were recorded, according to the method of Rosenthale et al., Int. Arch. Pharmacol., 172, 91 (1968). The bronchoconstrictor agent acetylcholine (ACH) was administered at doses of 10 to 40 mcg./kg. depending on each animal's sensitivity to this compound, and control responses to acetylcholine were thus established. Bronchoconstrictor agents raise the resistance of the lungs to inflation thereby decreasing the tidal air flow. 7-(2β-[(3S)-3-Ethynyl-3-hydroxy-trans-1-octenyl]-3α-hydroxy-5-oxo-1α-cyclopentyl)-cis-5-heptenoic acid was then administered by aerosol, and the animals were then challenged again with acetylcholine, and the degree of inhibition of bronchoconstriction was thus determined. A minimum of two animals was used at each dose.

| Total Aerosol Dose (meg.) | Results[a] Mean % Protection VS ACH Bronchoconstriction |
|---|---|
| $1.5 \times 10^{-5}$ | 17 |
| $10^{-4}$ | 63 |
| $10^{-3}$ | 76 |
| $10^{-2}$ | 100 |
| $10^{-1}$ | 98 |

[a] Minimum of 2 animals per dose.

EXAMPLE 10

Anesthetized (Dial-urethane) guinea pigs were artificially respired at a constant positive air pressure (Starling miniature pump) and changes in tidal air during inspiration were recorded, according to the method of Rosenthale et al., Int. Arch. Pharmacol., 172, 91 (1968). The bronchoconstrictor agent acetylcholine (ACH) was administered at doses of 10 to 40 mcg./kg. depending on each animal's sensitivity to this compound, and control response to acetylcholine was thus established. Bronchoconstrictor agents raise the resistance of the lungs to inflation thereby decreasing the tidal air flow. 2β-[(3S)-3-Ethynyl-3-hydroxy-trans-1-octenyl]-3α-hydroxy-5-oxo-1α-cyclopentane-heptanoic acid was then administered by aerosol, and the animals were then challenged again with acetylcholine, and the degree of inhibition of bronchoconstriction was thus determined. A minimum of two animals was used at each dose.

| Total Aerosol Dose (meg.) | Results[a] Mean % Protection VS ACH Bronchoconstriction |
|---|---|
| $1.5 \times 10^{-6}$ | 0 |
| $10^{-5}$ | 38 |
| $10^{-4}$ | 60 |
| $10^{-3}$ | 84 |
| $10^{-2}$ | 90 |
| $10^{-1}$ | 100 |
| $10^{-0}$ | 98 |

[a] Minimum of 2 animals per dose.

EXAMPLE 11

Male Charles River rats weighing 200–300 g. are deprived of food but not water for 24 hours prior to use. Water is, however, withheld during the experiment. The rats are weighed, anesthetized with ether and the pylorus ligated according to the method of Shay et al., Gastroenterology, 26, pp. 906–913 (1954). Treatment of vehicle control is then administered interduodenally (i.d.). Rats are housed 2/cage and sacrificed with $CO_2$ four hours after ligation. The stomachs are removed, rinsed, and contents emptied into a graduated centrifuge tube. The tubes are centrifuged for 20 minutes at 20,000 R. P. M. and the volume of gastric juice recorded. Any samples obviously contaminated by feces, food or hemolysis are eliminated. An aliquot of each is frozen for later determination of $Na^+$, $K^+$ and $Cl^-$ concentration. The pH is measured and 1 ml. of gastric juice is titrated with 0.1 N NaOH to a pH of 7.0–7.4. The data are analyzed by either a Student's t-test or an analysis of variance depending upon which test is appropriate.

When tested in this fashion 7-(2β-[(3S)-3-ethynyl-3-hydroxy-trans-1-octenyl]-3α-hydroxy-5-oxo-1α-cyclopentyl)-cis-5-heptenoic acid gives the results indicated at the dose levels shown.

| Dose | Results |
|---|---|
| 0.5, 0.25 and 0.1 mg./kg. | Statistical significant decrease in total volume, vol./100 g. and total secreted milliequivalents but no change in weight, pH, $H^+Na^+$, $K^+$ or $Cl^-$ meq. |

When tested in this fashion, 2β-[(3S)-3-ethynyl-3-hydroxy-trans-1-octenyl]-3α-hydroxy-5-oxo-1α-cyclopentane-heptanoic acid gives the results indicated at the dose level shown.

| Dose | Result |
|---|---|
| 0.5 mg./kg. | Statistically significant decrease in vol./100 g. |

EXAMPLE 12

Female Charles River mice weighing between 18–24 g. are randomly divided into groups of 10 and dosed orally with the test compound in an aqueous vehicle. The mice are placed in individual plastic cages and observed for diarrhea at 15, 30, and 60 minutes.

The Diarrhea Dose 50% (DD-50) is calculated by finney's method of probits.

When tested by this method 7-(2β[(3S)-3-ethynyl-3-hydroxy-trans-1-octenyl]-3α-hydroxy-5-oxo-1α-cyclopentyl)-cis-5-heptenoic acid gives the following results.

DD-50 = 2.6 mg./kg.
(0.5 − 16.8)
slope = 1.36
g = 0.79

The subject matter which the applicant regards at his invention is particularly pointed out and distinctly claimed as follows:

1. A compound of the formula:

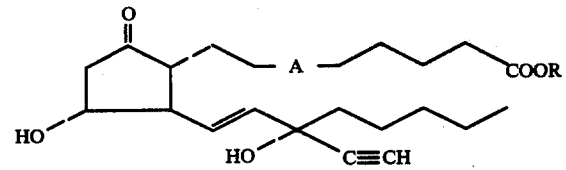

wherein A is a single bond; and R is hydrogen, alkyl of from 1 up to about 6 carbon atoms, alkali metal, or a pharmacologically acceptable cation derived from ammonia or a basic amine.

2. A compound as defined in claim 1 wherein A is a single bond.

3. A compound as defined in claim 2 which is 2β-[(3S)-3-ethynyl-3-hydroxy-trans-1-octenyl]-3α-hydroxy-5-oxo-1α-cyclopentane-heptanoic acid.

* * * * *